(12) United States Patent
Chen et al.

(10) Patent No.: US 9,771,324 B2
(45) Date of Patent: Sep. 26, 2017

(54) CHEMICAL FILM ON SUBSTRATE, METHOD OF FORMING THE SAME, AND METHOD OF FORMING N-HYDROXYSUCCINIMIDE ESTER-FUNCTIONALIZED PARACYCLOPHANE

(71) Applicant: Hsien-Yeh Chen, Taipei (TW)

(72) Inventors: Hsien-Yeh Chen, Taipei (TW); Chih-Hao Chang, Taipei (TW); Chiao-Tzu Su, Taipei (TW); Chun-Pin Lin, Taipei (TW); Jen Jang, Taipei (TW)

(73) Assignee: Hsien-Yeh Chen, Taipei (TW)

( * ) Notice: Subject to any disclaimer, the term of this patent is extended or adjusted under 35 U.S.C. 154(b) by 642 days.

(21) Appl. No.: 14/265,377

(22) Filed: Apr. 30, 2014

(65) Prior Publication Data

US 2015/0191628 A1 Jul. 9, 2015

(30) Foreign Application Priority Data

Jan. 6, 2014 (TW) .............................. 103100440 A

(51) Int. Cl.
| | | |
|---|---|---|
| *C07D 207/46* | (2006.01) | |
| *C09D 179/08* | (2006.01) | |
| *C23C 16/44* | (2006.01) | |
| *C23C 16/30* | (2006.01) | |
| *B05D 1/00* | (2006.01) | |
| *C08G 61/02* | (2006.01) | |

(52) U.S. Cl.
CPC .............. *C07D 207/46* (2013.01); *B05D 1/60* (2013.01); *C08G 61/025* (2013.01); *C23C 16/30* (2013.01); *C08G 2261/142* (2013.01); *C08G 2261/143* (2013.01); *C08G 2261/3424* (2013.01); *C08G 2261/592* (2013.01); *C08G 2261/598* (2013.01); *Y10T 428/31623* (2015.04); *Y10T 428/31681* (2015.04); *Y10T 428/31721* (2015.04)

(58) Field of Classification Search
CPC ...... C07D 207/46; C09D 179/08; C23C 16/44
See application file for complete search history.

(56) References Cited

U.S. PATENT DOCUMENTS 7,947,148 B2    5/2011   Lahann

OTHER PUBLICATIONS

Jen Jang, Vapor-Based Synthesis of N-hydroxysuccinimide ester Functionalized Poly-p-xylylene and Its Use for Biointerface Modifications (ntu-102-R00524051), Jul. 2013.

*Primary Examiner* — Sun Jae Yoo
(74) *Attorney, Agent, or Firm* — Winston Hsu

(57) ABSTRACT

The present invention provides a method of forming N-hydroxysuccinimide ester-functionalized paracyclophane. The present method is carried out by adding 4-carboxyl-paracyclophane into N,N'-Dicyclohexylcarbodiimide (DCC) and N-Hydroxysuccinimide (NHS) to form N-hydroxysuccinimide ester-functionalized paracyclophane. The present invention further provides a chemical film on a substrate and a method of forming the same, wherein the chemical film includes N-hydroxysuccinimide ester-functionalized poly-para-xylylene.

8 Claims, 9 Drawing Sheets

CHEMICAL FILM ON SUBSTRATE, METHOD OF FORMING THE SAME, AND METHOD OF FORMING N-HYDROXYSUCCINIMIDE ESTER-FUNCTIONALIZED PARACYCLOPHANE

BACKGROUND OF THE INVENTION

1. Field of the Invention

The present invention relates to a chemical film of N-hydroxysuccinimide ester-functionalized poly-para-xylylene on substrates, a method of forming the same chemical film of N-hydroxysuccinimide ester-functionalized poly-para-xylylene, and a method of forming the precursor, N-hydroxysuccinimide ester-functionalized paracyclophane, and more particularly, to a chemical film of N-hydroxysuccinimide ester-functionalized poly-para-xylylene formed by chemical vapor deposition, a forming method thereof, and a method of forming the precursor, N-hydroxysuccinimide ester-functionalized paracyclophane.

2. Description of the Prior Art

Reactions and interactions which occur on a surface of a material, as well as the structure and composition of the material as observed from the surface, are greatly different from what can be seen from a macroscopic view. Although those in the field have studied responses to various materials for many years, especially in the field of biomedical interface science, interface science is still considered revolutionary. In the last half century, rapid development of equipment facilitated the development of interface science, material science, and bioscience, which has enabled people in the field to analyze surface compositions of bio-molecular structures. Accordingly, the current status of interface science is well set to study physical and chemical phenomena that occur at the surface or interface of two phases and two cells. Recent reports have demonstrated that surface characteristics are significantly related to biological performances such as protein bond and cytogenesis.

In conventional arts, chemical vapor deposition (CVD) is regarded as one of the best synthesizing systems to prepare poly-para-xylylenes. Prepared poly-para-xylylenes have the characteristics of biocompatibility, biostability, moisture-proofing, chemical resistance, and dielectric property. Conventional poly-para-xylylene coated film does not have any anchor compound which can receive other molecules for additional modification, however, and is poor when used as a connection compound for other biomolecules. Although plenty of methods have been developed to prepare functional groups that can be used as an anchor compound in the modification process, as well as further modifying the poly-para-xylylene coated film, it is still limited in practical use.

N-hydroxysuccinimide ester (NHS ester) is regarded as a significant functional group in biomaterials science, due to the cross-linkage between the N-hydroxysuccinimide ester and the primary amine in peptides and proteins. Conventional arts lack a proper method of synthesizing N-hydroxysuccinimide ester-functionalized poly-para-xylylene, however, as well as a proper CVD process to deposit the N-hydroxysuccinimide ester-functionalized poly-para-xylylene on a substrate.

SUMMARY OF THE INVENTION

It is therefore one of the objectives of the present invention to provide a method of synthesizing N-hydroxysuccinimide ester-functionalized paracyclophane, a method of forming a chemical film comprising N-hydroxysuccinimide ester-functionalized poly-para-xylylene on a substrate, and a chemical film comprising N-hydroxysuccinimide ester-functionalized poly-para-xylylene on a substrate, so as to provide a preferable synthesizing system for biomaterials.

In accordance with an embodiment of the present invention, the present invention provides a method of forming N-hydroxysuccinimide ester-functionalized paracyclophane. The method comprises adding 4-carboxyl-paracyclophane to N,N'-Dicyclohexylcarbodiimide (DCC) and N-Hydroxysuccinimide (NHS) to obtain N-hydroxysuccinimide ester-functionalized paracyclophane.

In accordance with another embodiment of the present invention, the present invention provides a method of forming a chemical film on a substrate. The method first provides a substrate, and then carries out a chemical vapor deposition (CVD) process to form a chemical film on the substrate, wherein the chemical film comprises N-hydroxysuccinimide ester-functionalized poly-para-xylylene. The CVD process is carried out at less than 10 Pascal (Pa).

In accordance with another embodiment of the present invention, the present invention provides a chemical film on a substrate, wherein the chemical film comprises N-hydroxysuccinimide ester-functionalized poly-para-xylylene, and the chemical film is deposited on a substrate.

The present invention provides a method of forming N-hydroxysuccinimide ester-functionalized paracyclophane, which can utilize the CVD process to prepare the aforementioned chemical film, and N-hydroxysuccinimide ester-functionalized poly-para-xylylene to conjugate biomolecules for additional modifications. Various primary amines can then be bound to the film comprising N-hydroxysuccinimide ester-functionalized poly-para-xylylene through a fast, stable and highly affined bioconjucation reaction. The present invention is thereby able to fix biomolecules having an amine group on the chemical film.

These and other objectives of the present invention will no doubt become obvious to those of ordinary skill in the art after reading the following detailed description of the preferred embodiment that is illustrated in the various figures and drawings.

DETAILED DESCRIPTION

To provide a better understanding of the present invention, preferred embodiments are detailed as follows. The preferred embodiments are also illustrated in the accompanying drawings to clarify the contents and effects of the present invention.

Figure 1:
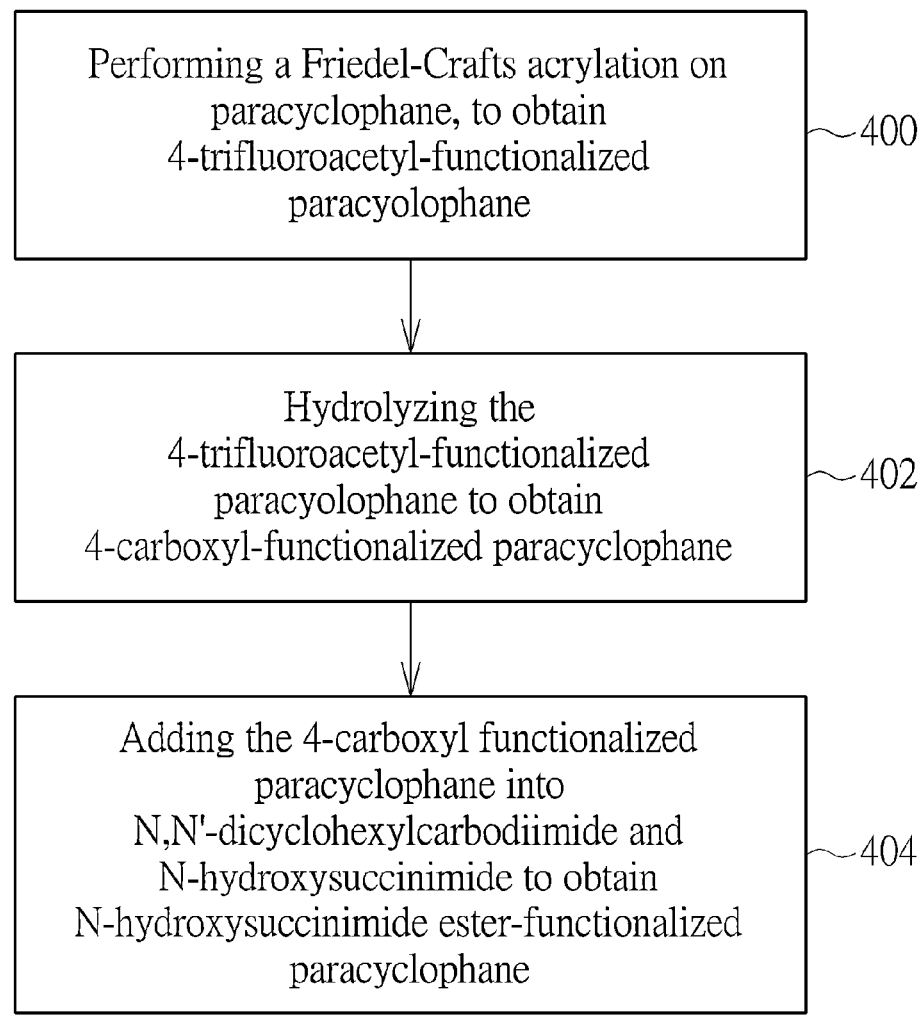
FIG. 1 is a flow chart illustrating a method of forming N-hydroxysuccinimide ester-functionalized paracyclophane.

FIG. 1 is a flow chart illustrating a method of forming N-hydroxysuccinimide ester-functionalized paracyclophane. As shown in FIG. 1, the method of forming N-hydroxysuccinimide ester-functionalized paracyclophane in the present invention comprises performing a Friedel-Crafts acrylation on paracyclophane to obtain 4-trifluoroacetyl-functionalized paracyolophane (Step 400). In one embodiment of the present invention, the Friedel-Crafts acrylation is carried out by adding trifluoroacetic anhydride and aluminum oxide ($AlCl_3$) as a catalyst.

Next, the 4-trifluoroacetyl-functionalized paracyolophane is hydrolyzed to obtain 4-carboxyl-functionalized paracyclophane (Step 402). In one embodiment, the hydrolyzing of the 4-trifluoroacetyl-functionalized paracyolophane is carried out by adding a hydroxide, such as potassium hydroxide (KOH), into 4-trifluoroacetyl-functionalized paracyolophane.

Finally, the 4-carboxyl functionalized paracyclophane is added into N,N'-dicyclohexylcarbodiimide (DCC) and N-hydroxysuccinimide (NHS) to obtain the N-hydroxysuccinimide ester-functionalized paracyclophane (Step 404). The N-hydroxysuccinimide ester-functionalized paracyclophane may comprise formula (1) or formula (2) as illustrated below:

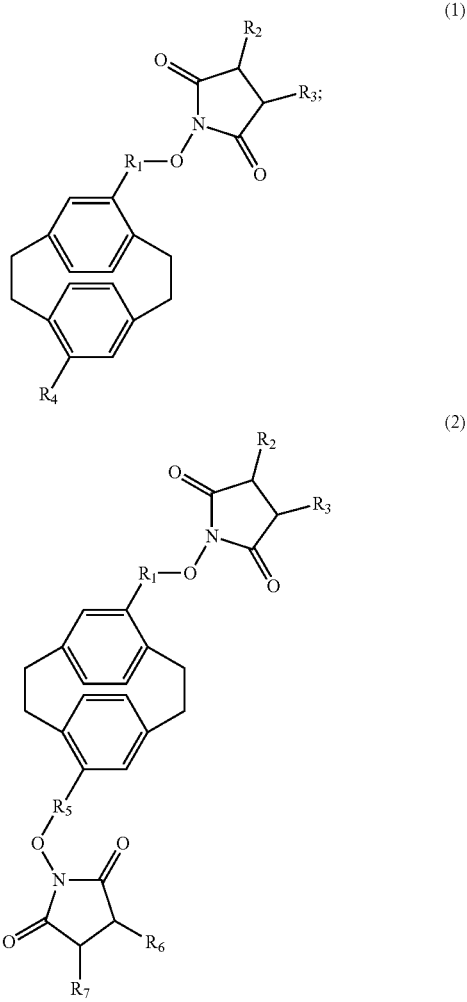

Wherein, "R1" and "R5" refers to —$CH_2$—, —$CH_2$—$CH_2$—OC(=O)—, —$CH_2$—$CH_2$—NH—C(=O)—, —C(=O)— or —O—$CH_2$— respectively and "$R_2$", "$R_3$", "$R_4$", "$R_6$", and "$R_7$" refers to hydrogen, methyl (Me) or chlorine, respectively.

Through the aforementioned processes, the N-hydroxysuccinimide ester-functionalized paracyclophane having the formula as shown in formula (1) or formula (2) can be obtained. In the following paragraphs, each step of the method will be further detailed using N-hydroxysuccinimide ester-functionalized [2.2]paracyclophane as an example.

As shown in step 400, 40 grams (g) of poly-para-xylene [as shown in formula (3)] is disposed in a flat-bottom bin connected to a vacuum-pumping and nitrogen-filling apparatus. Overnight vacuum pumping is performed to remove moisture to obtain a moisture free poly-para-xylene. It is noted that the vacuum-pumping and nitrogen-filling apparatus must be supplied with enough nitrogen during the vacuum pumping. Then, 1200 milliliters (ml) of dichloromethane (DCM) is dissolved in water gradationally and kept at 0° C. water bath. 54 ml of trifluoroacetic anhydride and aluminum chloride ($AlCl_3$) are then added to the dichloromethane and mixed with each other. The mixture is stirred for 15 minutes, followed by adding the moisture free poly-para-xylene gradationally over 15 minutes. This mixture is kept at 0° C. for 90 minutes to obtain a reactant. After that, 35 ml hydrochloric acid (HCl), distilled water (DI-water), and 1N sodium hydroxide are added to the reactant to extract a crude 4-trifluoroacety-[2.2]paracyclophane in an organic horizon. The organic horizon is then collected and mixed with anhydrous ($MgSO_4$), and the water therein is filtered out to obtain an extract. The extract is further purified through a column chromatography process by using an eluent having DCM/hexane (1:2). Finally, purified 4-trifluoroacety-[2.2]paracyclophane [as shown in formula (4)] in white and solid are obtained, with a yield of 95%.

Formula (3) and formula (4) are illustrated below:

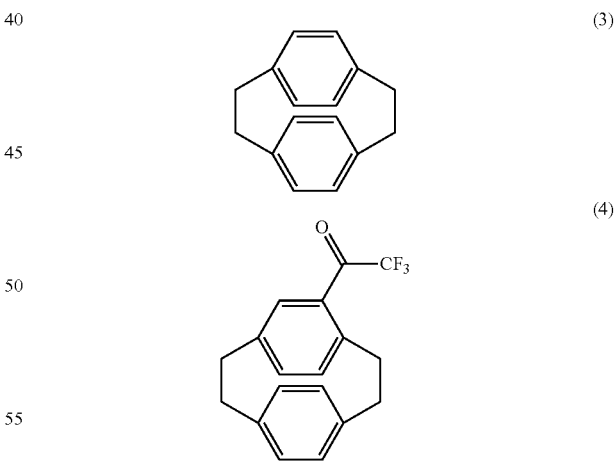

In step 402, 56 g of the 4-trifluoroacety-[2.2]paracyclophane [as shown in formula (4)], 1.25 liter (L) and 10% potassium hydroxide are mixed and heated for 3.5 hours to dissolve the 4-trifluoroacety-[2.2]paracyclophane. A reflux condensation process is then performed for 1 hour, precipitated with hydrochloric acid (HCl), and filtrated through a suction filtration process, to obtain 37.5 g of 4-carboxyl[2,2]paracyclophane [as shown in formula (5)] in white and solid, with a yield of 85%.

Wherein formula (5) is illustrated below:

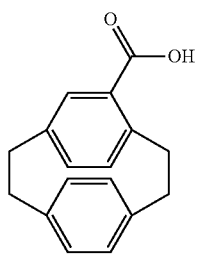

(5)

3 g of the 4-carboxyl[2,2]paracyclophane [as shown in formula (5)] are dissolved in tetrahydrofuran (THF), mixed with N,N'-dicyclohexylcarbodiimide (DCC) for 20 minutes, and then further mixed with N-hydroxysuccinimide (NHS) for 16 hours. Resultant sediments are filtered out to collect supernatant liquid, which is further purified through a column chromatography process by using an eluent having EA/hexane (1:2) and a thin layer chromatography (TLC) film (Rf=0.5) to obtain 2.4 g of purified N-hydroxysuccinimide ester-functionalized [2,2]paracyclophane in light yellow and solid [as shown in formula (6)], with a yield of 80%.

Formula (6) is illustrated below:

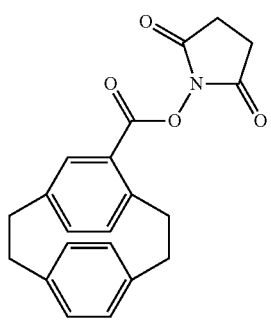

(6)

Figure 2:
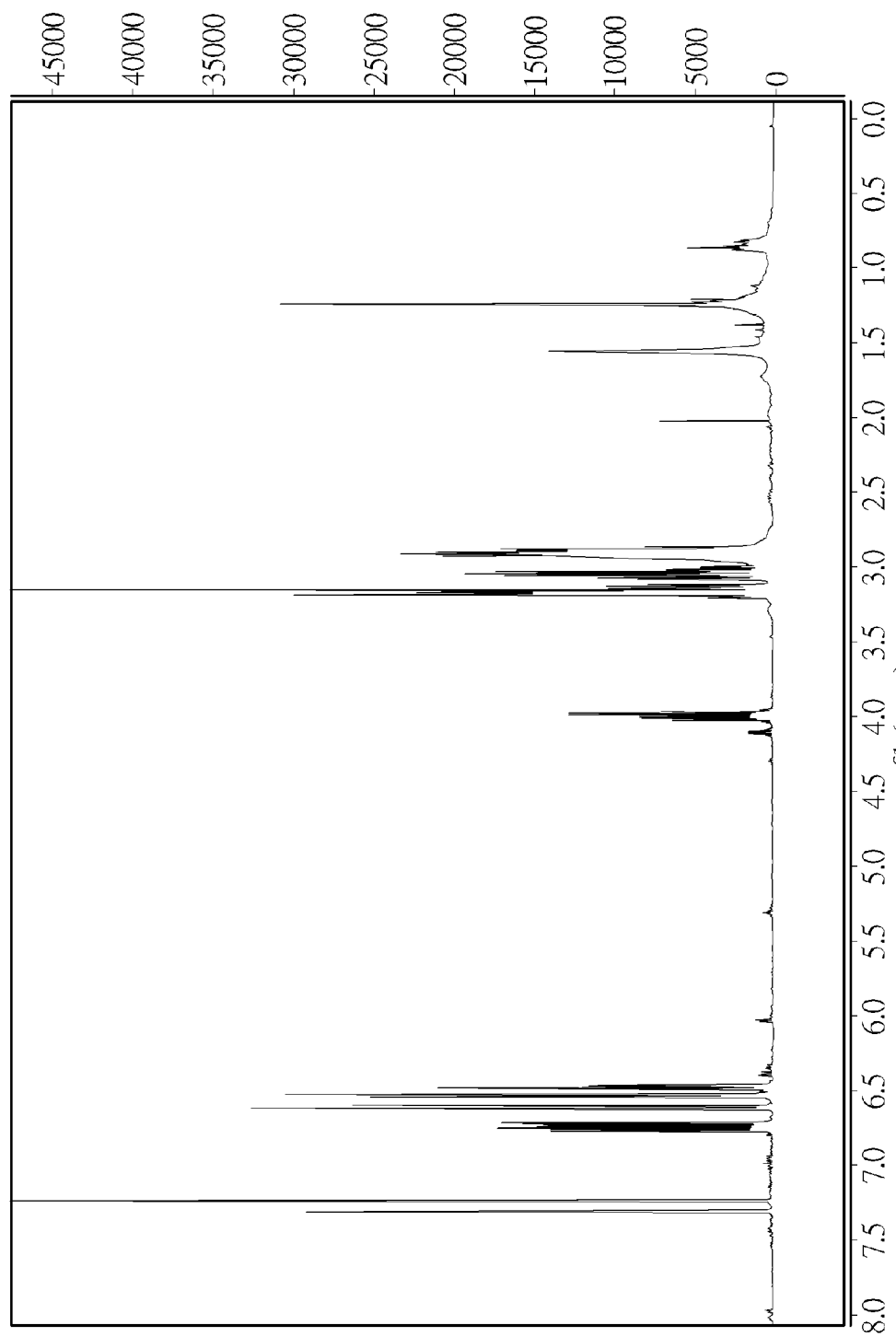
FIG. 2 is a $^1$H NMR spectrum of N-hydroxysuccinimide ester-functionalized paracyclophane.
Figure 3:
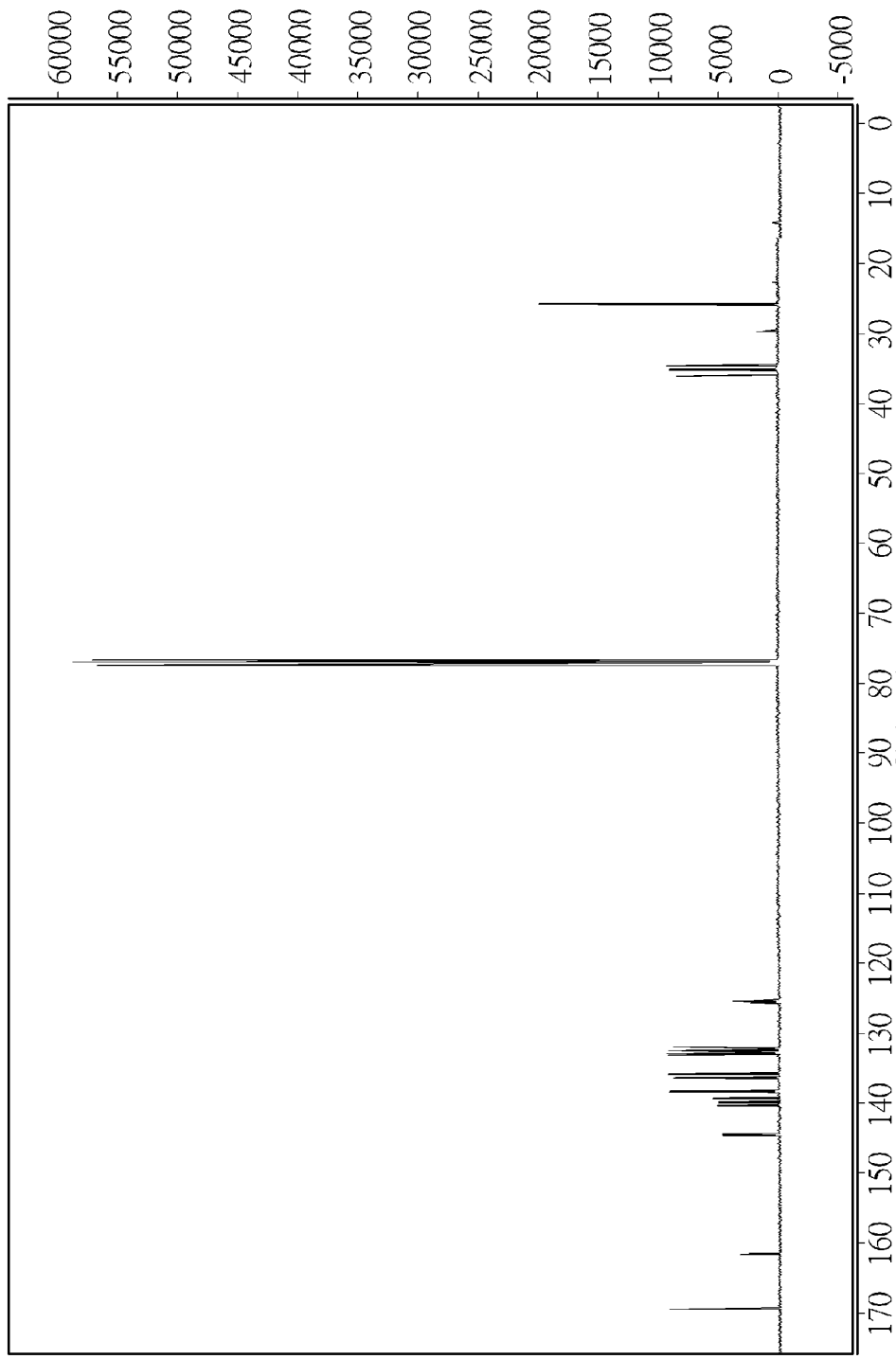
FIG. 3 is a $^{13}$C NMR spectrum of N-hydroxysuccinimide ester-functionalized paracyclophane.
Figure 4:
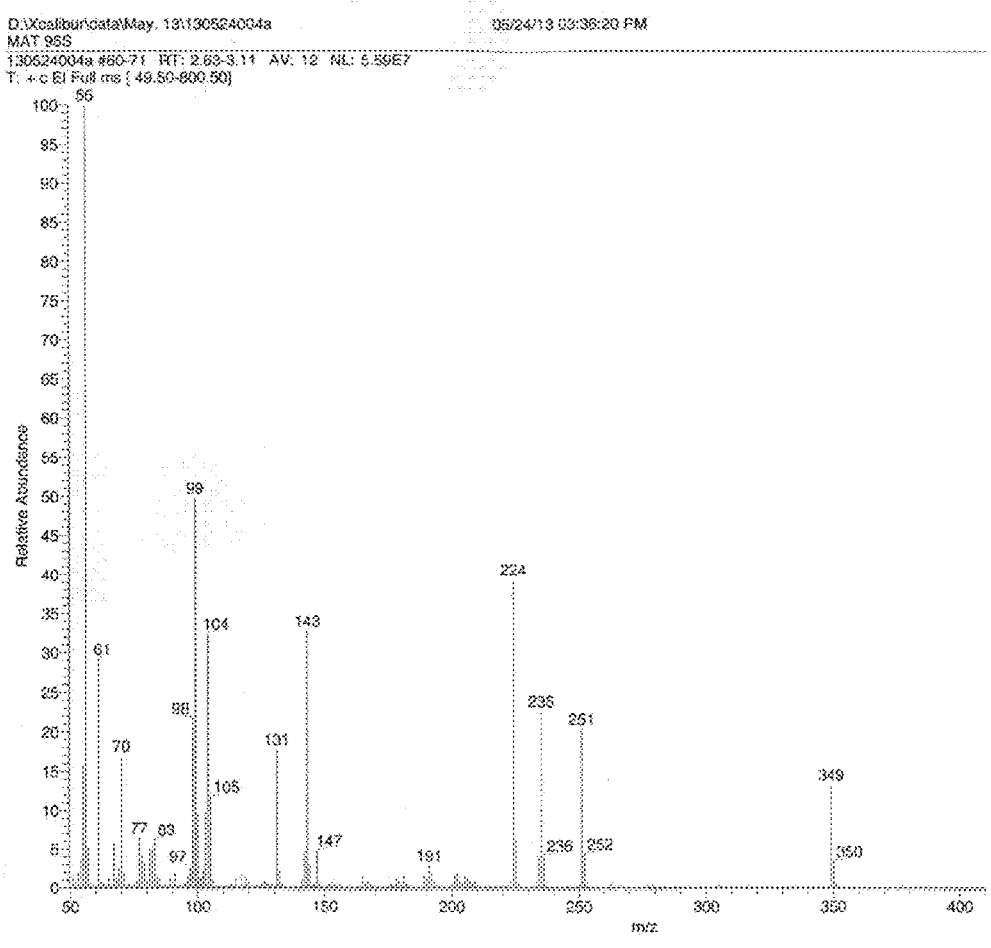
FIG. 4 is a mass spectrometry (MS) spectrum of N-hydroxysuccinimide ester-functionalized paracyclophane.

Through the aforementioned steps, the N-hydroxysuccinimide ester-functionalized paracyclophane, for example N-hydroxysuccinimide ester-functionalized paracyclophane, can be obtained. The obtained N-hydroxysuccinimide ester-functionalized paracyclophane is then analyzed by NMR spectrum and mass spectrometry (MS) spectrum. Please refer to FIG. 2, FIG. 3 and FIG. 4. FIG. 2 is a $^1$H NMR spectrum of N-hydroxysuccinimide ester-functionalized paracyclophane, FIG. 3 is a $^{13}$C NMR spectrum of N-hydroxysuccinimide ester-functionalized paracyclophane, and FIG. 4 is a mass spectrometry (MS) spectrum of N-hydroxysuccinimide ester-functionalized paracyclophane. As shown in FIG. 2, "2.85-2.95 (4H; CH$_2$)" refers to the four hydrogen atoms of N-hydroxysuccinimide. $^1$H NMR (300 MHz, CDCl3, TMS): δ=2.85-2.95 (4H; CH2), 2.92-2.99 (1H; CH2), 3.07-3.23 (6H; CH2), 4.10 (1H; CH2), 6.51 (1H; CH), 6.54 (1H; CH), 6.60 (1H; CH), 6.65 (1H; CH), 6.68 (1H; CH), 6.81 (1H; CH), 7.39 (1H; CH). As shown in FIG. 3, $^{13}$C NMR spectrum: 13C NMR: 25.77, 34.55, 35.08, 35.22, 36.06, 76.78, 77.03, 77.29, 125.51, 132.08, 132.55, 132.91, 133.03, 135.92, 136.46, 138.41, 139.38, 139.84, 140.45, 144.62, 162.64, 169.56. As shown in FIG. 4, a maximum signal is observed at "349" which is equal to the molecular weight of the N-hydroxysuccinimide ester-functionalized paracyclophane. With such spectra data, it is demonstrated that the method of forming N-hydroxysuccinimide ester-functionalized paracyclophane according to the present invention can obtain N-hydroxysuccinimide ester-functionalized paracyclophane as products.

As shown in reaction (1) illustrated below, the obtained N-hydroxysuccinimide ester-functionalized paracyclophane can be further polymerized through a pyrolysis process, and then coated on a substrate through a chemical vapor deposition (CVD) process to form a chemical film comprising N-hydroxysuccinimide ester-functionalized poly-para-xylylene.

Reaction 1

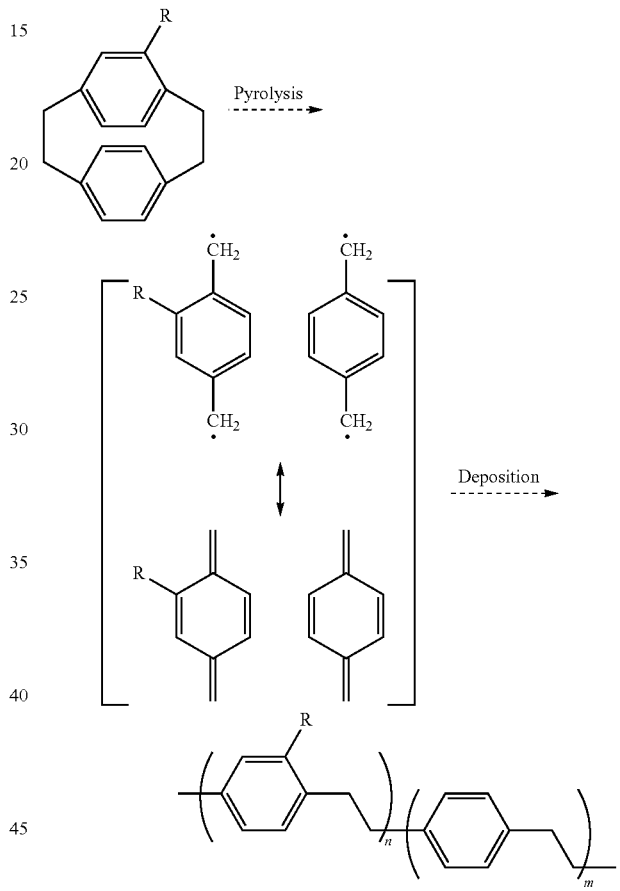

Wherein the N-hydroxysuccinimide ester-functionalized poly-para-xylylene can comprise formula (7) or formula (8) as illustrated below:

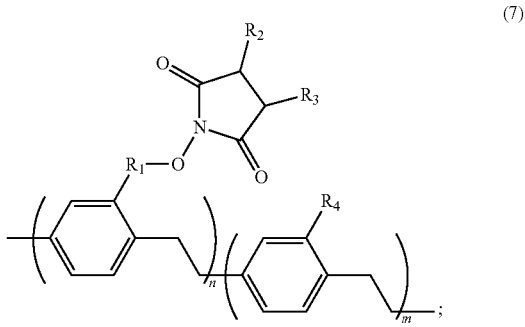

(7)

-continued

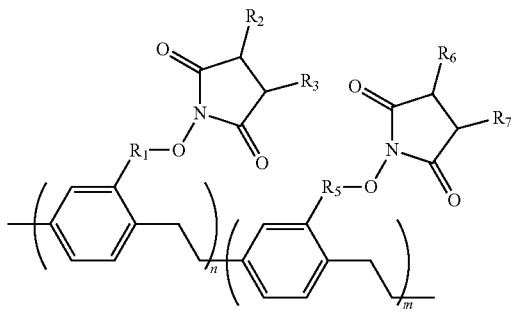

(8)

Wherein, "R1" and "R5" refers to —C(═O)—, —CH$_2$—C(═O), CH$_2$—OC(═O)—, —CH$_2$—CH$_2$—NH—C(═O)—, or —O—CH$_2$— respectively, R$_2$, R$_3$, R$_4$, R$_6$, and R$_7$ refers to hydrogen, methyl (Me), or chlorine respectively, and "m" and "n" refers to an integral greater than 15000 respectively, and m:n can be any ratio, such as 1:1, 1:2, 1:3 and so on; preferably 1:1 but it is not limited thereto.

Figure 5:
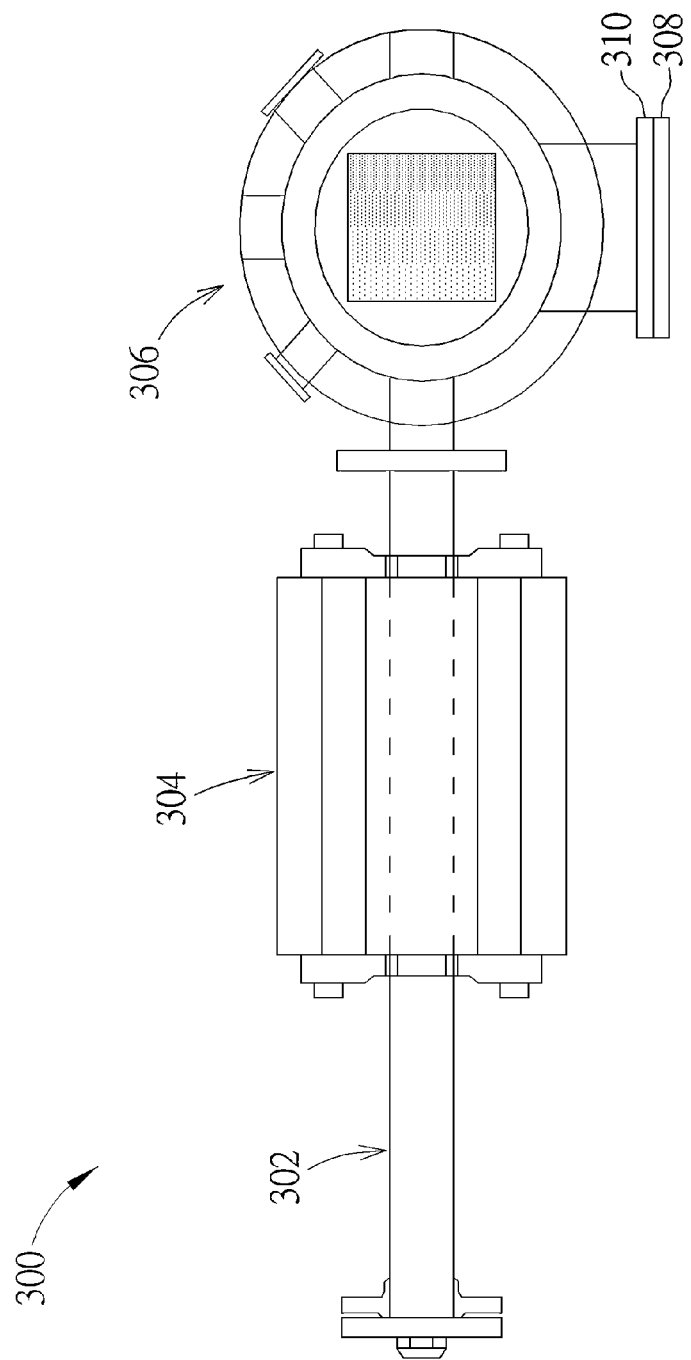
FIG. 5 is a diagram illustrating a chemical vapor deposition system used in the present invention.

FIG. 5 is a diagram illustrating a chemical vapor deposition system used in the present invention. As shown in FIG. 5, the chemical vapor deposition system 300 comprises a sublamination zone 302, a pyrolysis zone 304, and a deposition chamber 306. The N-hydroxysuccinimide ester-functionalized paracyclophane is inhaled from the sublamination zone 302, undergoes a pyrolysis process in the pyrolysis zone 304, and is then deposited on a substrate 308 placed on the deposition chamber 306. In this way, a chemical film 310 comprising the N-hydroxysuccinimide ester-functionalized poly-para-xylylene is obtained.

In one embodiment of the present invention, the chemical vapor deposition system 300 utilizes argon as the delivery gas to adjust systemic pressure, wherein the pressure of the chemical vapor deposition system 300 is adjusted to 100 mTorr, and the chamber is heated to 90° C. to prevent the poly-para-xylylene (precursor) from being deposited on the chamber. The sublimation temperature of the paracyclophane is kept at 100 to 150° C., the sedimentation rate is adjusted to 0.5 Å/s via a quartz crystal microbalance (QCM), and the pyrolysis temperature is 600° C. The substrate 308 is placed on a bearer having a room temperature, such as 20° C., wherein the bearer is self-rotated to provide uniform coating of around 150 micrometers on the substrate 308. In one embodiment of the present invention, the substrate 308 can be any material capable of being used in the chemical vapor deposition process, such as a semiconductor, ceramics, glass, metal or any composition thereof. The semiconductor can be silicon or germanium. The glass can optionally be any doped glass or undoped glass. The metal can be copper (Cu), silver (Ag) or titanium (Ti), and can also be alloy, such as titanium alloy (Ti6Al4V). The composition can be any resin polymer, such as polystyrene (PS), or polymethylmethacrylate (PMMA). The substrate 308 can be a combination of the aforementioned materials, such as a silicon substrate having a silver film, but is not limited thereto. In another embodiment of the present invention, the substrate 308 can be a biological duct, stent, or pacemaker, but is not limited thereto.

It is noted that, in view of the stability of the N-hydroxysuccinimide ester functional group, the pressure of the chemical vapor deposition system 300 of the present invention can be further adjusted to achieve preferable quality of the chemical film 310 comprising N-hydroxysuccinimide ester-functionalized poly-para-xylylene. As an example, the chemical vapor deposition system 300 can be performed at a circumstance of less than 10 Pascal (Pa), preferably less than 1 Pa, and more preferably between $10^{-4}$ and $10^{-5}$ Pa. The pyrolysis process and the following deposition process can therefore be performed at a lower temperature. In the present embodiment, the pyrolysis process can be performed at 500° C. to 520° C. to form the chemical film 310 comprising N-hydroxysuccinimide ester-functionalized poly-para-xylylene, due to the vacuum environment used in the method of the present invention. The N-hydroxysuccinimide ester functional group is more stable during the processes used in the method of the present invention, and will not be pyrolysed during these processes. Furthermore, the chemical film 310 comprising N-hydroxysuccinimide ester-functionalized poly-para-xylylene can be formed at a lower temperature (5° C.-15° C., preferably at 5° C.-10° C.), which is also due to the vacuum environment used in the method of the present invention. Therefore, the chemical film 310 will be of a good quality.

Further referring to FIG. 5, in one practical embodiment, the chemical vapor deposition system 300 further comprises a turbomolecular pump to create a vacuum environment at $10^{-8}$ Pa, and to inhale 20 sccm/min argon flows for maintaining the systemic pressure at $10^{-4}$-$10^{-5}$ Pa. In such a condition, the N-hydroxysuccinimide ester-functionalized paracyclophane in the sublamination zone 302 is heated (around 100° C.) and sublimated, and then delivered to the pyrolysis zone 304 (around 500° C.) through the delivery of the argon. The carbon chains of the [2.2]paracyclophane of the N-hydroxysuccinimide ester-functionalized paracyclophane will be pyrolysed to release free radicals, and the N-hydroxysuccinimide ester functional group will not be pyrolysed. Finally, the free radicals in a gaseous phase will spontaneously be deposited on the substrate 308 placed on the self-rotated bearer (around 5° C.-10° C.) in the deposition chamber 306, to obtain the chemical film 310 comprising N-hydroxysuccinimide ester-functionalized poly-para-xylylene. In the present embodiment, the deposition rate can be monitored through the demonstration of the quartz crystal microbalance (QCM) disposed in the chemical vapor deposition system 300, wherein the deposition rate of the present practical embodiment is around 0.5 Å/s.

Figure 6:
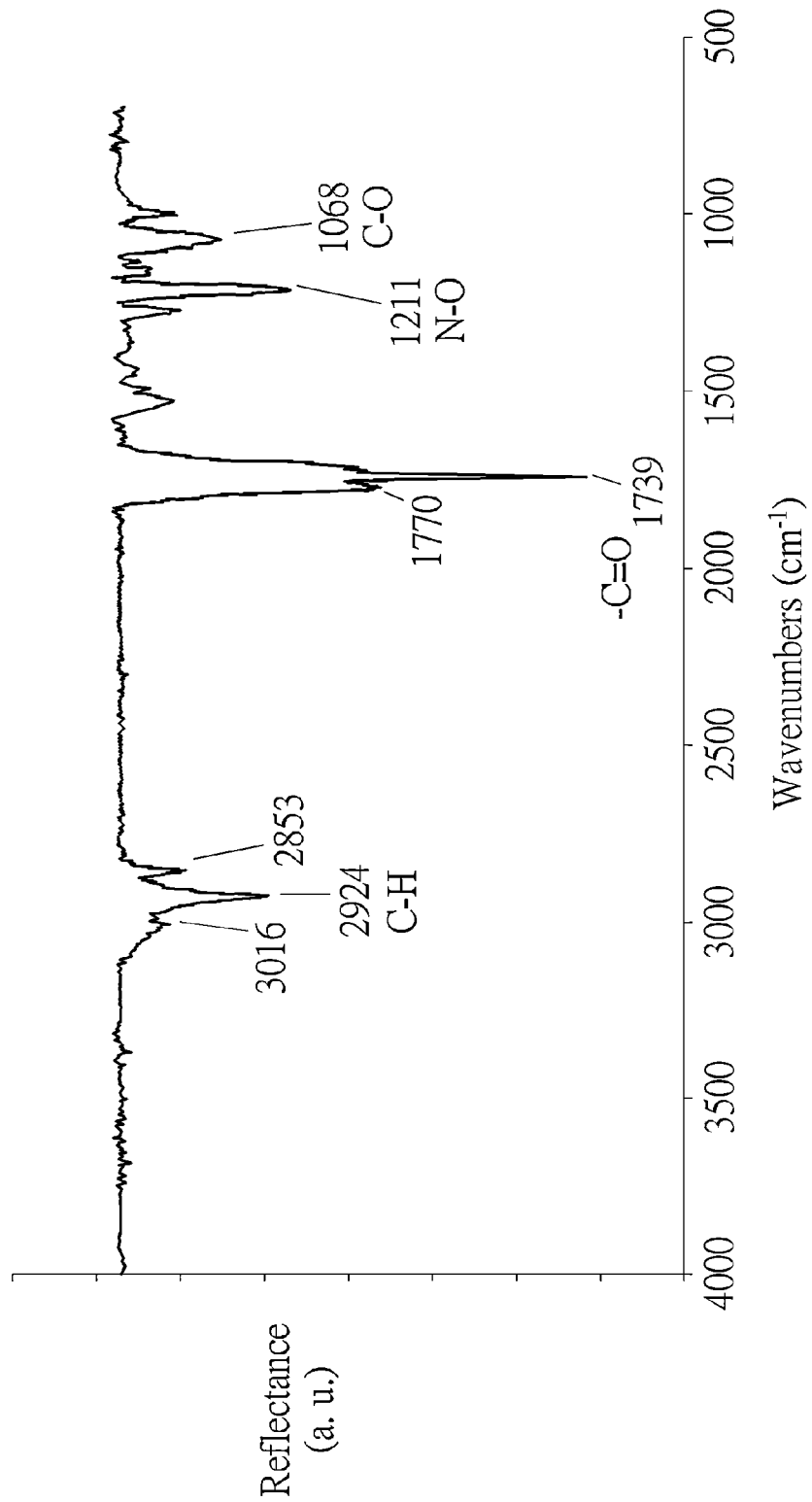
FIG. 6 is a Fourier transform infrared spectroscopy spectrum of a chemical film comprising N-hydroxysuccinimide ester-functionalized poly-para-xylylene.
Figure 7:
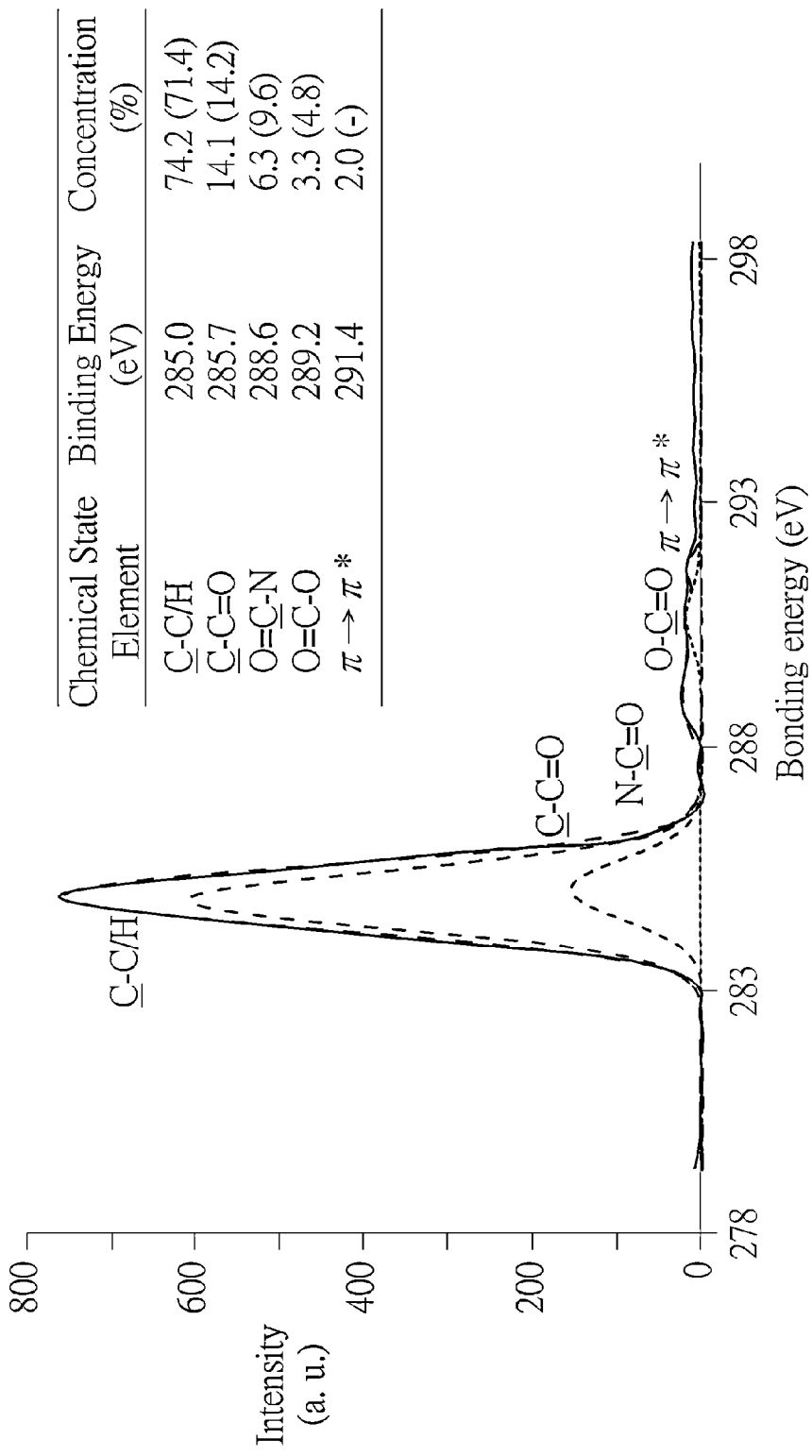
FIG. 7 is an X-ray photoelectron spectroscopy (XPS) spectrum of a chemical film comprising N-hydroxysuccinimide ester-functionalized poly-para-xylylenes.

After the aforementioned processes, the obtained chemical film 310 comprising N-hydroxysuccinimide ester-functionalized poly-para-xylylene, for example, poly[(4-carboxylic acid N-hydroxysuccinimide ester-p-xylylene)-co-(p-xylylene)], can be analyzed through a Fourier transform infrared spectroscopy (FT-IR) and X-ray photoelectron spectroscopy (XPS), to ensure the structure of the chemical film 310 comprising N-hydroxysuccinimide ester-functionalized poly-para-xylylene and the completeness of the N-hydroxysuccinimide ester functional group of the chemical film 310. FIG. 6 is a Fourier transform infrared spectroscopy spectrum of the chemical film comprising N-hydroxysuccinimide ester-functionalized poly-para-xylylene, and FIG. 7 is an X-ray photoelectron spectroscopy (XPS) spectrum of the chemical film comprising N-hydroxysuccinimide ester-functionalized poly-para-xylylene. As shown in FIG. 6, the infrared reflection-absorption spectroscopy (IRRAS) spectrum shows carbonyl bond (C═O) of succinimide group in the region 1810 cm$^{-1}$, 1780 cm$^{-1}$, carbonyl bond (C═O) of ester in the region 1737 cm$^{-1}$ and C—O bond in the region 1708 cm$^{-1}$, and N—O bond in the region 1210 cm$^{-1}$. The N-hydroxysuccinimide ester functional group of the chemical film 310 comprising N-hydroxysuccinimide ester-functionalized poly-para-xylylene will not be pyrolysed during the processes. FIG. 7 shows the same results. A thickness of the chemical film 310 can be measured by using an ellipsometer, wherein the thickness of the chemical film 310 of the present invention is around 10 nanometers (nm) to 25 micrometers (μm).

Figure 8:
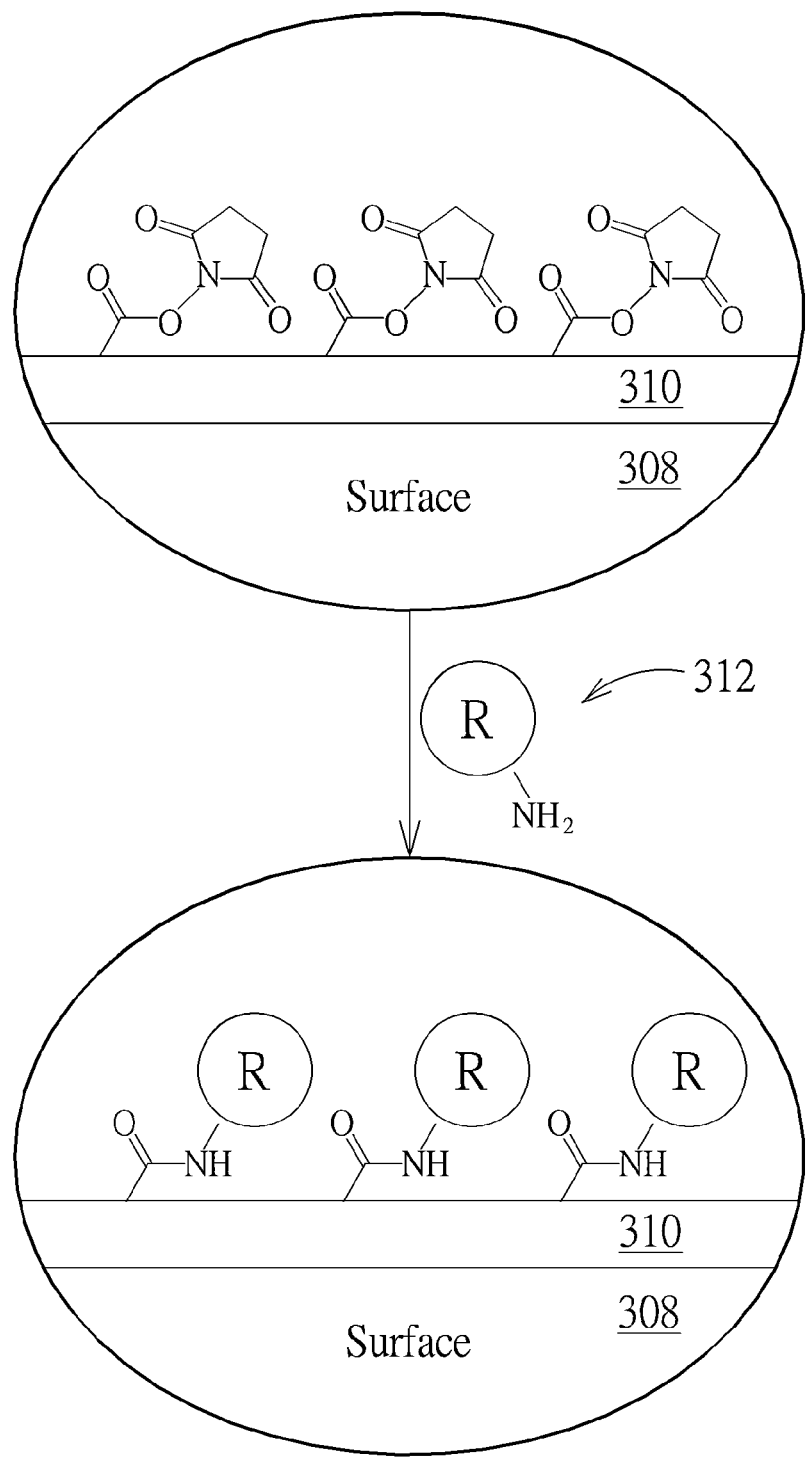
FIG. 8 is a diagram illustrating a process of anchoring a molecule having primary amines on a chemical film comprising N-hydroxysuccinimide ester-functionalized poly-para-xylylene in the present invention.

After forming the stable chemical film 310 comprising N-hydroxysuccinimide ester-functionalized poly-para-xylylene, the chemical film 310 can be further modified through many possible treatments, such as cross-linkage with any biomolecules. In one embodiment of the present invention, the N-hydroxysuccinimide ester-functionalized poly-para-xylylene of the chemical film 310 can cross-link with a target molecule, for example a primary amine, wherein the target molecule is anchored on the chemical film 310 comprising the N-hydroxysuccinimide ester-functionalized poly-para-xylylene. FIG. 8 is a diagram illustrating a process of anchoring a molecule having primary amines in the chemical film 310 comprising N-hydroxysuccinimide ester-functionalized poly-para-xylylene. As shown in FIG. 8, the molecular having primary amine (R—NH$_2$) 312 is anchored in the chemical film 310 via the interaction between the molecular and the N-hydroxysuccinimide ester-functionalized poly-para-xylylene of the chemical film 310.

Figure 9:
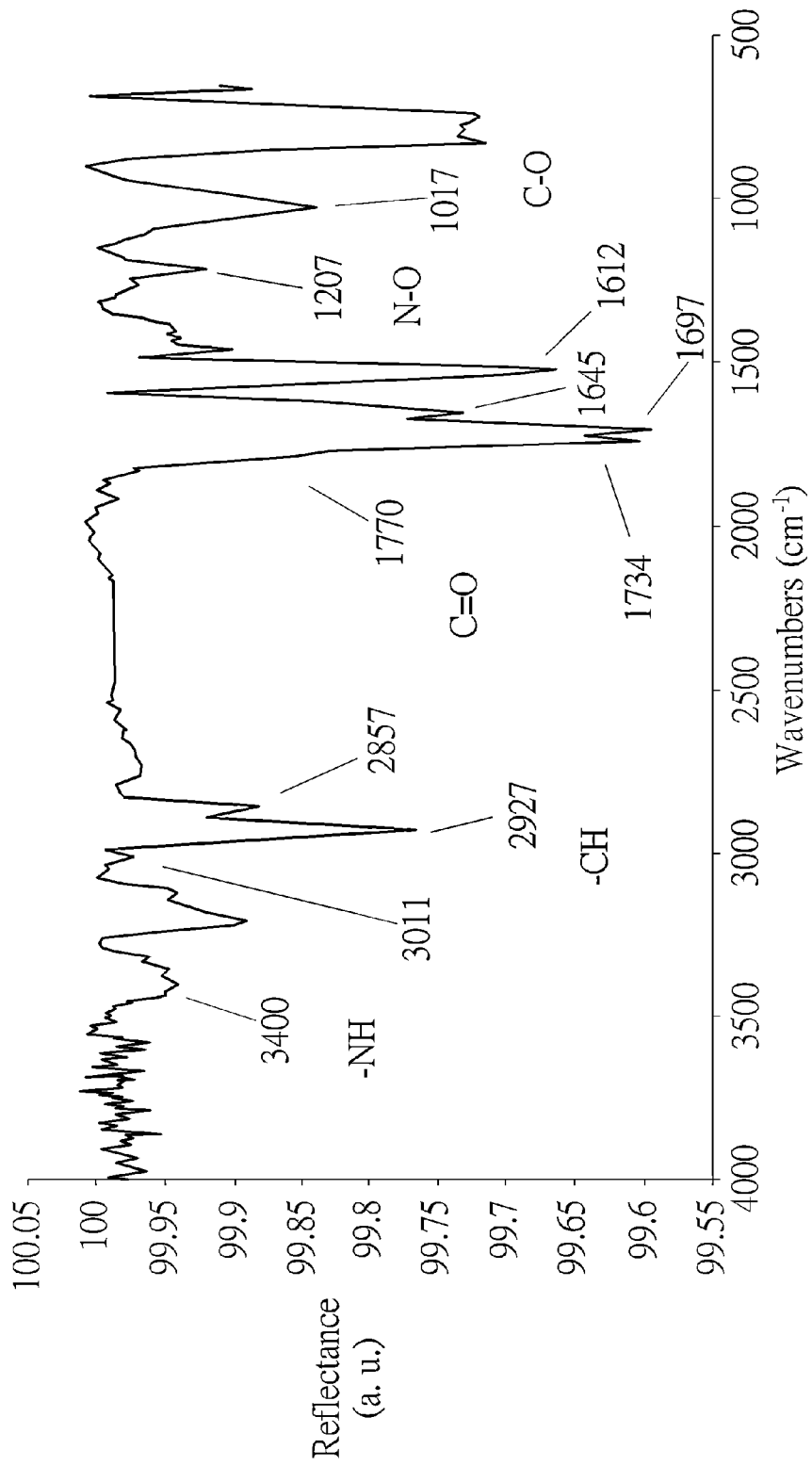
FIG. 9 is an infrared reflection-absorption spectroscopy (IRRAS) spectrum of a cycloheximide (CHX) modified chemical film comprising N-hydroxysuccinimide ester-functionalized poly-para-xylylene illustrating the bonding between the CHX and the N-hydroxysuccinimide ester-functionalized poly-para-xylylene coated on the chemical film.

In a preferred embodiment of the present invention, the anchoring of the molecular which has primary amine 312 in the chemical film 310 further comprises cycloheximide (CHX), wherein the cycloheximide is used for sterilization by destroying a bacteria's cell membrane. In the present embodiment, the cycloheximide is formulated with phosphate buffer (PBS) to obtain a reagent in 10 micromolar (mM). Then, 10 μl of the reagent is dropped on a silicon chip having the chemical film 310 comprising N-hydroxysuccinimide ester-functionalized poly-para-xylylene for 2 hours, followed by washing the silicon chip with PBS buffer [including 0.02% (v/v) Tween 20, 0.1% (w/v) bovine serum albumin (BSA)] and distilled water, and drying with nitrogen. After that, the silicon chip is surface analyzed through IRRAS. FIG. 9 is an infrared reflection-absorption spectroscopy (IRRAS) spectrum of a cycloheximide (CHX) modified chemical film comprising N-hydroxysuccinimide ester-functionalized poly-para-xylylene illustrating the bonding between CHX and the N-hydroxysuccinimide ester-functionalized poly-para-xylylene of the chemical film. As shown in FIG. 9, the IRRAS spectrum shows N—H bond of CHX in the region 3400 cm-1, carbonyl bond (C=O) of succinimide group in the region 1770 cm$^{-1}$, carbonyl bond (C=O) of ester in the region 1734 cm$^{-1}$, C—O bond in the region 1017 cm$^{-1}$, and N—O bond in the region 1207 cm$^{-1}$. The figure illustrates that the CHX is anchored in the chemical film 310.

It is also noted that the target molecule and the molecule having primary amine 312 is not limited to CHX, and can be any molecule that is able to react with the chemical film 310 comprising N-hydroxysuccinimide ester-functionalized poly-para-xylylene. In one embodiment, the primary amine 312 can be a fouling resistance molecule, such as polyethylene glycol (PEG) or ethanolamine. In another embodiment, the primary amine can be an antibacterial molecule, chlorhexidine (CHX) or epigallocatechin gallate (EGCG). In another embodiment, the primary amine can be a protein, such as vascular endothelial growth factor (VEGF), bone morphogenetic proteins (BMP-2), or testes-specificprotein 50 (TSP50). In other embodiments, the primary amine can be other peptides.

In summary, the present invention provides a method of forming N-hydroxysuccinimide ester-functionalized paracyclophane, which can utilize the CVD process to prepare the aforementioned chemical film, and N-hydroxysuccinimide ester-functionalized poly-para-xylylene to conjugate biomolecules for additional modifications. In this way, various primary amines can be bound to the N-hydroxysuccinimide ester-functionalized poly-para-xylylene of the chemical film through a fast, stable and highly affined bioconjucation reaction. The present invention is therefor able to fix biomolecules of an amine group on the chemical film.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of forming N-hydroxysuccinimide ester-functionalized paracyclophane, comprising:
adding 4-carboxyl-functionalized paracyclophane to N,N'-Dicyclohexylcarbodiimide (DCC) and N-Hydroxysuccinimide (NHS) to form N-hydroxysuccinimide ester-functionalized paracyclophane.

2. The method of forming N-hydroxysuccinimide ester-functionalized paracyclophane according to claim 1, wherein the 4-carboxyl-functionalized paracyclophane is obtained by hydrolyzing 4-trifluoroacetyl-functionalized paracyolophane to obtain the 4-carboxyl-functionalized paracyclophane.

3. The method of forming N-hydroxysuccinimide ester-functionalized paracyclophane according to claim 2, wherein the hydrolyzing process further comprises adding a hydroxide.

4. The method of forming N-hydroxysuccinimide ester-functionalized paracyclophane according to claim 3, wherein the hydroxide comprises potassium hydroxide (KOH).

5. The method of forming N-hydroxysuccinimide ester-functionalized paracyclophane according to claim 2, wherein the 4-trifluoroacetyl-functionalized paracyolophane is obtained by performing a Friedel-Crafts acrylation reaction on paracylophane to obtain the 4-trifluoroacetyl-functionalized paracyolophane.

6. The method of forming N-hydroxysuccinimide ester-functionalized paracyclophane according to claim 5, wherein the Friedel-Crafts acrylation reaction comprises adding trifluoroacetatic anhydride.

7. The method of forming N-hydroxysuccinimide ester-functionalized paracyclophane according to claim 5, wherein the Friedel-Crafts acrylation reaction comprises adding aluminum oxide.

8. The method of forming N-hydroxysuccinimide ester-functionalized paracyclophane according to claim 1, wherein the N-hydroxysuccinimide ester-functionalized paracyclophane has formula (a) or formula (b):

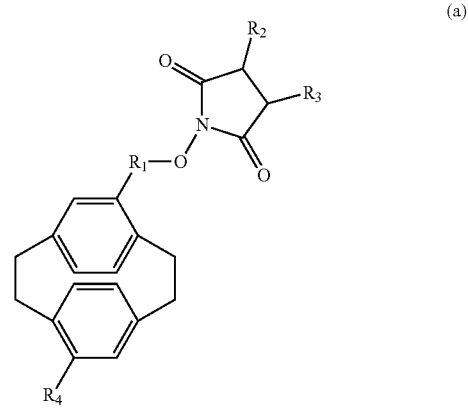

(a)

-continued
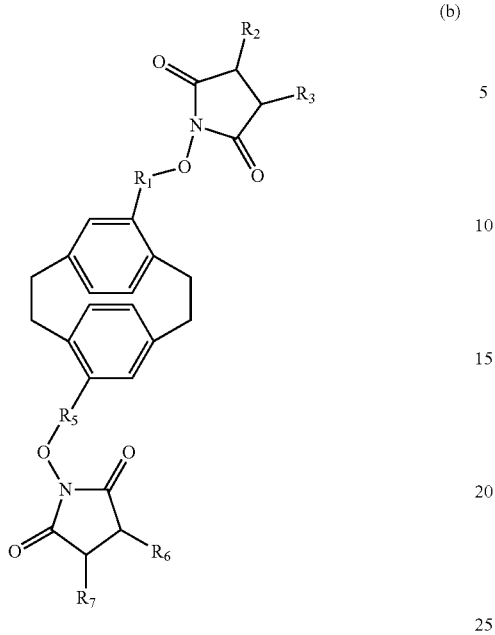
(b)
wherein, $R_1$ and $R_5$ refers to $-CH_2-$, $-CH_2-CH_2-OC(=O)-$, $-CH_2-CH_2-NH-C(=O)-$, $-C(=O)-$ or $-O-CH_2-$ respectively and $R_2$, $R_3$, $R_4$, $R_6$, and $R_7$ refers to hydrogen, methyl (Me), or chlorine, respectively.
* * * * *